United States Patent [19]

Heller

[11] Patent Number: 4,639,366

[45] Date of Patent: Jan. 27, 1987

[54] POLYMERS CONTAINING PENDANT ACID FUNCTIONALITIES AND LABILE BACKBONE BONDS

[75] Inventor: Jorge Heller, Woodside, Calif.

[73] Assignee: Merck & Co., Inc., Rahway, N.J.

[21] Appl. No.: 618,002

[22] Filed: Jun. 6, 1984

[51] Int. Cl.[4] .................... A61K 31/74; A61K 31/765

[52] U.S. Cl. ........................................ 424/19; 424/20; 424/22; 424/78

[58] Field of Search ........................ 424/22, 78, 19, 20

[56] References Cited

U.S. PATENT DOCUMENTS

| | | | |
|---|---|---|---|
| 4,093,709 | 6/1978 | Choi et al. | 424/19 |
| 4,150,108 | 4/1979 | Graham | 424/22 |
| 4,221,779 | 9/1980 | Graham | 424/78 |
| 4,304,767 | 12/1981 | Heller et al. | 424/78 |

*Primary Examiner*—John Kight
*Assistant Examiner*—M. L. Moore
*Attorney, Agent, or Firm*—R. Brent Olson; Manfred Polk; Michael C. Sudol, Jr.

[57] ABSTRACT

The instant invention is directed to a polymer with at least one labile backbone bond per repeat unit and at least one pendant acid functionality per thousand repeat units.

The instant invention is also directed to a controlled release device which comprises:

(A) a polymer with at least one labile backbone bond per repeat unit and at least one pendant acid functionality per thousand repeat units; and (B) a beneficial substance incorporated within or surrounded by the matrix of said polymer.

4 Claims, No Drawings

POLYMERS CONTAINING PENDANT ACID FUNCTIONALITIES AND LABILE BACKBONE BONDS

BACKGROUND OF THE INVENTION

There has long been a need in the field of drug delivery devices to have a drug released in the human or animal tissue at the place where it is most therapeutically effective and to have said drug released in the tissue in a controlled manner over a long period of time.

U.S. Pat. Nos. 4,093,709 and 4,304,767 disclose polymers which can be used as a matrix to contain a drug. The polymers contain labile backbone bonds which hydrolyze in the presence of water causing a controlled erosion of the matrix and resultant release of the drug. These polymers have the disadvantage, however, that they hydrolyze extremely slowly.

The polymers of the instant invention have the advantage that the pendant acid functionalities catalyze the hydrolysis of the labile polymer backbone bonds.

DESCRIPTION OF THE INVENTION

The instant invention is directed to a polymer with at least one labile backbone bond per repeat unit and at least one pendant acid functionality per thousand repeat units.

The instant invention is also directed to a controlled release device which comprises:

(A) a polymer with at least one labile backbone bond per repeat unit and at least one pendant acid functionality per thousand repeat units; and (B) a beneficial substance incorporated within or surrounded by the matrix of said polymer.

The polymers of the instant invention may be prepared by reacting a polyol, preferably a diol, having a pendant acidic group with a polymer containing a labile backbone bond. Excess amounts of either component may be used in preparing the final polymer, although stoichiometric amounts are preferred.

U.S. Pat. Nos. 4,093,709 and 4,304,767, which are hereby incorporated by reference, disclose numerous polyols. Any of these polyols may be modified to contain one or more pendant acidic groups per thousand repeat units, up to a maximum of one per repeat unit. The number of acid groups incorporated depends on the desired rate of erosion. For increased erosion, relatively more acid groups would be incorporated. A preferred group of polyols may be represented as follows:

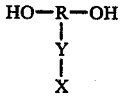

where X is the acidic group and Y is a spacer group. R and Y may be an alkyl, aryl or substiuted alkyl or aryl, preferably containing 1 to 18 carbon atoms, most preferably 2 to 10 carbon atoms. The Y group may optionally be eliminated.

Any acidic group may be used in the polyol. Examples include carboxylic, carbon acid, phosphoric, sulfonic and sulfenic acid groups.

Tri- and higher hydroxyl functional polyols may be used, which will result in crosslinked polymers.

Any polymer containing at least one acid labile backbone bond per repeat unit (preferably two per repeat acid unit) may be used to react with the polyol containing a pendant acid group. Examples include polyorthoesters (including polyorthocarbonates), polyacetals, polyketals, polyesters and polyphosphazenes. The preferred polymers are poly(orthoesters) and polyacetals. Examples of polyorthoesters, polyorthocarbonates and polyacetals are disclosed in U.S. Pat. No. 4,093,709, and U.S. Pat. Nos. 4,304,767, 4,221,779 and 4,150,108 which are hereby incorporated by reference.

The preparation of the polymers may be by a variety of methods. U.S. Pat. No. 4,093,709, column 8, line 11 through column 9, line 47, outlines several methods of preparation.

Any beneficial substance (e.g. therapeutics or biologically active agents) may be used in the controlled release device. The substance should not significantly interfere with the acid catalyzed hydrolysis of the labile polymer backbone bond. Basic substances may cause some interference. It is preferred that any acid substances be in the salt form.

Representative examples of the polyols are as follows: 9,10-dihydroxystearic acid; 3,6-dihydroxynaphthalene-2,7-disulfonic acid; 2,4-dihydroxybenzoic acid; 3,4-dihydroxycinnamic acid; 6,7-dihydroxy-2-naphthalene sulfonic acid; 6,7-dihydroxy-2-naphtalene sulfenic acid; 2,5-dihydroxyphenylacetic acid; 2,4-dihydroxypyrimidine-5-carboxylic acid; 4,8-dihydroxyquinoline-2-carboxylic acid; and mixtures thereof.

It will be realized that these are merely representative examples and that any polyol containing an acidic group can be used provided it does not adversely affect the polymerization reaction or leads to toxicologically undesirable degradation products. Thus, any group that can be incorporated into the polymer and which when placed in water ionizes to produce a pH lower than about 7.0 is a useful group provided the above limitations are met.

The molecular weight of the polymer is not critical. The molecular weight is preferably at least 1,000 as determined by low angle light scattering.

Representative beneficial substances (therapeutics and biologically active agents) for incorporation into or to be surrounded by the polymer matrix to be used with this invention and to be released to an aqueous environment include without limitation, the following:

1. Protein drugs such as insulin;

2. Desensitizing agents such as ragweed pollen antigens, hay fever pollen antigens, dust antigen and milk antigen;

3. Vaccines such as smallpox, yellow fever, distemper, hog cholera, fowl pox, antivenom, scarlet fever, dyptheria toxoid, tetanus toxoid, pigeon pox, whooping cough, influenzae, rabies, mumps, measles, poliomyelitis, Newcastle disease, etc.;

4. Anti-infectives, such as antibiotics, including penicillin, tetracycline, chlortetracycline bacitracin, nystatin, streptomycin, neomycin, polymyxin, gramicidin, oxytetracycline, chloramphenicol, and erythromycin; sulfonamides, including sulfacetamide, sulfamethizole, sulfamethazine, sulfadiazine, sulfamerazine, and sulfisoxazole, cefoxitin; anti-virals including idoxuridine; and other anti-infectives including nitrofurazone and sodium propionate;

5. Antiallergenics such as antazoline, methapyrilene, chlorpheniramine, pyrilamine and prophenpyridamine;

6. Steroidal anti-inflammatory agents such as hydrocortisone, cortisone, hydrocortisone acetate, dexamethasone, dexamethasone 21-phosphate, fluocinolone, triamcinolone, medrysone, prednisolone, prednisolone 21-phosphate, and prednisolone acetate;

7. Decongestants such as phenylephrine, naphazoline, and tetrahydrazoline;

8. Miotics such as pilocarpine, eserine salicylate, carbachol, diisopropyl fluorophosphate, phospholine iodide, and demecarium bromide;

9. Anticholinergics such as atropine sulfate, cyclopentolate, homatropine, scopolamine, tropicamide, eucatropine, and hydroxyamphetamine;

10. Sympathomimetics such as epinephrine;

11. Sedatives and Hypnotics such as pentabarbital sodium, phenobarbital, secobarbital sodium, codeine, (α-bromoisovaleryl)urea, carbromal;

12. Psychic Energizers such as 3-(2-aminopropyl)indole acetate, 3-(2-aminobutyl)indole acetate and amitriptyline;

13. Tranquilizers such as reserpine, chlorpromazine, thiopropazate and perphenazine;

14. Androgenic steroids such as methyltestosterone and fluorymesterone;

15. Estrogens such as estrone, 17 β-estradiol, ethinyl estradiol, and diethyl stilbesterol;

16. Progestational agents such as progesterone, megestrol, melengestrol, chlormadinone, ethisterone, norethynodrel, 19-nor-progesterone, norethindrone, medroxyprogesterone and 17 β-hydroxy-progesterone;

17. Humoral agents such as the prostaglandins, for example $PGE_1$, $PGE_2$ and $PGF_2$;

18. Antipyretics analgesics such as aspirin, sodium salicylate, salicylamide, and diflunisal;

19. Antispasmodics such as atropine, methantheline, papaverine, and methscopolamine bromide;

20. Antimalarials such as the 4-aminoquinolines, 8-aminoquinolines, chloroquine, and pyrimethamine;

21. Antihistamines such as diphenhydramine, dimenhydrinate, tripelennamine, perphenazine, and chlorophenazine;

22. Cardioactive agents such as dibenzhydroflumethiazide, flumethiazide, hydrochlorothiazide chlorothiazide, and aminotrate;

23. Non-steroidal anti-inflammatory agents such as indomethacin and sulindac;

24. Antiparkinsonian agents such as L-dopa;

25. Antihypertensive agents such as methyldopa;

26. β-Adrenergic blocking agents such as propanolol and timolol;

27. Nutritional agents such as vitamins, essential amino acids and essential fats.

Other drugs having the same or different physiological activity as those recited above can be employed in drug-delivery systems within the scope of the present invention.

Other benificent compounds which can be released in a controlled manner over time can also be incorporated in the present invention. These include but are not limited to herbicides, pesticides, fertilizers, antifouling agents, biocides (germacides). One skilled in the art would realize that any beneficial substances which are released to the aqueous atmosphere can be used in this invention.

Drugs or therapeutically beneficial substances can be in various forms, such as uncharged molecules, components of molecular complexes, or nonirritating, pharmacologically acceptable salts such as hydrochloride, hydrobromide, sulfate, phosphate, nitrate, borate, acetate, maleate, tartrate, salicylate, etc. For acidic drugs, salts of metals, amines, or organic cations (e.g., quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug or beneficial substance incorporated into the polymer matrix will vary greatly depending on the particular drug, the desired therapeutic effect and the time span in which the polymer matrix is eroded to release the particular drug. Thus, there is no critical upper limit on the amount of drug incorporated in the polymer matrix and the lower limit will also depend on the activity of the drug (usually at least 0.1%, preferably 0.1 to 30%, by weight, based on the total weight of the device) and the time span for the erosion of the polymer and subsequently the drug release. Thus, it is not practical to define a range for the therapeutically effective amount of drug to be incorporated in the novel polymer matrixes of the instant invention.

Also in the case of the drug or other beneficial substance incorporated into the polymer matrix as stated above, the amount of drug or beneficial substance will depend on the type of drug or substance for the condition being treated and can generally be up to 70% of the polymer matrix by weight.

The drug or other beneficial substance can be administered in various ways and shapes. For example, the polymer/drug or beneficial substance can be incorporated into disc-shaped devices, rods or sheets for under the skin implantation, spherical shapes and the like. Those skilled in the art would realize that the invention can be incorporated in any shaped device for the particular application it is being used for.

The above described devices can be prepared by, for example:

1. Methods of preparation include: (1) Dissolution of components in solvent, evaporation of solvent, compression of matrix; (2) Mechanical milling of polymer and drug or other beneficial substance followed by compression; (3) Melt mixing of polymer and drug or other beneficial substance. In all cases, after mixing, standard pharmaceutical technology is used to make the dosage form.

At least enough water must be present in contact with the polymer to cause degradation. Water in excess of this amount will not materially effect the performance of the invention.

When the polymer is exposed to water, the acid functionality of the polymer slowly catalyzes the hydrolysis of the labile backbone bond of the polymer, and the beneficial substance is released at a controlled rate.

EXAMPLE 1

16.30 g (0.113 moles) of trans-cyclohexanedimethanol, 8.15 g (0.069 moles) of 1,6-hexanediol and 11.08 g (0.035 moles) of 9,10-dihydroxystearic acid were dissolved in 350 ml of tetrahydrofuran in a 1 liter 3-necked round bottom flask equipped with an overhead stirrer, argon inlet and rubber septum. The mixture was heated with a heat-gun to about 35° C. to dissolve the 9,10-dihydroxystearic acid and 46.09 g (0.217 moles) of 3,9-bis(ethylidene)-2,4,8,10-tetraoxaspiro[5,5] undecane dissolved in 150 ml of tetrahydrofurn was transferred to the reaction flask through the rubber septum using argon pressure and a steel U-tube. Polymerization was initiated by adding 0.1 ml of a solution prepared by dissolving 0.29 g of p-toluenesulfonic acid in 10 ml of tetrahydrofuran. Polymer was isolated by precipitation into a large excess of methanol, filtering and vacuum drying.

EXAMPLE 2

Polymers containing smaller amounts of 9,10-dihydroxystearic acid were prepared by following the same procedure as in Example 1, but using the following amounts of monomers.

For polymer containing 4 mole % 9,10-dihydroxystearic acid 46.09 g (0.217 mole) 3,9-bis(ethylidene)-2,4,8,10-tetraoxaspiro[5,5]undecane, 17.59 g (0.122 moles) 1,4 transcyclohexanedimethanol, 9.22 g (0.078 mole) 1,6-henanediol and 5.38 g (0.017 mole) 9,10-dihydroxystearic acid.

EXAMPLE 3

Following the procedure of Example 1, 46.09 g (0.217 mole) 3,9-bis(ethylidene)-2,4,8,10-tetraoxaspiro[5,5] undecane was reacted with a mixture of 18.17 g (0.126 mole) 1,4-transcyclohexanedimethanol, 9.81 g (0.083 mole) 1,6-hexanediol and 2.85 g (0.009 mole) 9,10-dihydroxystearic acid.

EXAMPLE 4

Following the procedure of Example 1, 46.09 g (0.217 mole) of 3,9-bis (ethylidene)-2,4,8,10-tetraoxaspiro[5,5] undecane was reacted with a mixture of 24.57 g (0.208 mole) of 1,6-hexanediol and 1.64 g (0.009 mole) of 3,4-dihydroxycinnamic acid.

EXAMPLE 5

Following the procedure of Example 1, 46.09 g (0.217 mole) of 3,9-bis(ethylidene)-2,4,8,10-tetraoxaspiro[5,5]undecane was reacted with a mixture of 30.00 (0.208 mole) of trans-cyclohexanedimethanol and 2.36 g (0.009 mole) 6,7-dihydroxy-2-naphthalenesulfonic acid.

EXAMPLE 6

Following the procedure of Example 1, 46.09 g (0.217 mole) of 3,9-bis(ethylidene)-2,4,8,10-tetraoxaspiro[5,5]undecane was reacted with a mixture of 18.54 g (0.206 mole) of 1,4-butanediol and 1.72 g (0.011 mole) of 2,4-dihydroxypyrimidine-5-carboxylic acid.

EXAMPLE 7

Following the procedure of Example 1, 30.81 g (0.217 mole) of 1,4-divinyloxybutane was reacted with 21.53 g (0.207 mole) 1,5-pentanediol and 3.17 g (0.010 mole) 9,10-dihydroxystearic acid.

EXAMPLE 8

Following the procedure of Example 1, 34.29 g (0.217 mole) of diethylene glycol divinyl ether was reacted with 30.58 g (0.212 mole) of 1,4-trans-cyclohexanedimethanol and 1.82 g (0.005 mole) of 3,6-dihydroxynapthalene-2,7-disulfonic acid.

EXAMPLE 9

Finely ground polymer powders (480 mg), which contained 1 mole of 9,10-dihydroxystearic acid, 39.5 mole % of 1,6-hexanediol and 59.5 mole % of 1,4-transcyclohexanedimethanol, were mixed with 20 mg of monosodium ivermectin-4"-o-phosphate. Powders were compressed into pellet and injection-molded into sheets (0.8 mm in thickness). Discs (8 mm diameter) were punched off from the sheet. They were placed in 200 ml of pH 7.4 phosphate buffer solution and agitated vertically at a rate of 32 stroke/min at 37° C. The release of drug from the matrix was obtained over 320 hrs.

What is claimed is:

1. A polymer with at least one labile backbone bond per repeat unit and at least one pendant acid functionality per thousand repeat units.

2. The polymer of claim 1, wherein the backbone of the polymer is selected from the group consisting of polyorthoesters, polyacetals, polyketals, polyesters and polyphosphazenes.

3. The polymer of claim 1, wherein the pendant acid functionality is selected from the group consisting of carboxylic, phosphoric, sulfonic and sulfenic.

4. The polymer of claim 1, prepared from a diol containing a pendant acid functionality selected from the group consisting of 9,10-dihydroxystearic acid; 3,6-dihydroxynaphthalene-2,7-disulfonic acid; 2,4-dihydroxybenzoic acid; 3,4-dihydroxycinnamic acid; 3,4-dihydrocinnamic acid; 6,7-dihydroxy-2-naphtahalene sulfonic acid; 2,5-dihydroxyphenylacetic acid; 2,4-dihydroxypyrimidine-5-carboxylic acid; 4,8-dihydroxyquinoline-2-carboxylic acid; and mixtures thereof; and at least one additional monomer selected from the group consisting of esters, acetals and mixtures thereof.

* * * * *